United States Patent [19]

Valdivia et al.

[11] Patent Number: 5,698,219
[45] Date of Patent: Dec. 16, 1997

[54] NANOEMULSION OF THE OIL WATER TYPE, USEFUL AS AN OPHTHALMIC VEHICLE AND PROCESS FOR THE PREPARATION THEREOF

[75] Inventors: Francisco Javier Galan Valdivia; Anna Coll Dachs, both of Barcelona; Nuria Carreras Perdiguer, Caldes de Montbui, all of Spain

[73] Assignee: Laboratorios Cusi, S.A., Barcelona, Spain

[21] Appl. No.: 509,746

[22] Filed: Jul. 31, 1995

[30] Foreign Application Priority Data

Aug. 8, 1994 [ES] Spain ................................. 9401784

[51] Int. Cl.$^6$ ................................................ A61K 9/127
[52] U.S. Cl. ........................ 424/450; 436/829; 514/912
[58] Field of Search .......................... 424/450; 436/829; 514/912

[56] References Cited

U.S. PATENT DOCUMENTS

| | | |
|---|---|---|
| 2,832,721 | 4/1958 | Degkwitz . |
| 5,171,566 | 12/1992 | Grant . |
| 5,342,625 | 8/1994 | Hauer et al. ............................. 424/455 |
| 5,472,706 | 12/1995 | Friedman et al. ....................... 424/450 |

FOREIGN PATENT DOCUMENTS

| | | |
|---|---|---|
| 0 171 084 A3 | 8/1985 | European Pat. Off. . |
| 253472 | 1/1988 | European Pat. Off. . |
| 279241 | 8/1988 | European Pat. Off. . |
| 0 480 690 A1 | 10/1991 | European Pat. Off. . |
| 0 521 799 A1 | 3/1992 | European Pat. Off. . |
| WO 91/18669 | 12/1991 | WIPO . |
| WO 94/05298 | 3/1994 | WIPO . |

OTHER PUBLICATIONS

S. Benita & M.Y. Levy, "Submicron Emulsions as Colloidal Drug Carriers for Intravenous Administration: Comprehensive Physicochemical Characterization," Journal of Pharmaceutical Sciences, vol. 82, No. 11, Nov., 1993, 1069–1079.

E. Cotlier, M. Baskin & L. Kresca, "Effects of Lysophosphatidyl choline and phospholipase A on the Lens," Reports, vol. 14, No. 9, 697–701.

P.F. Kador & J.H. Konoshita, "Phospholipid Effects on the Rat Lens Transport System," Exp. Eye res. (1978), 26, 657–665.

I. Siebenbrodt & S. Keipert, "Poloxamer–Systems as Potential Ophthalmics," European Journal of Pharmaceutics and Biopharmaceutics, 39, Feb. 1993, No. 1, Stuttgart, DE, 25–30.

E. Sucker, P. Fuchs & P. Speiser, Pharmazeutische Technologie, Georg Thieme Verlag Stuttgart, New York, 1991, 644–654.

*Primary Examiner*—Carlos A. Azpuru
*Attorney, Agent, or Firm*—Klauber & Jackson

[57] ABSTRACT

A pharmaceutical vehicle which is a nanoemulsion is formulated using 0.1–10 % (w/v) of an oil; 0.1–10% (w/v) of a non-ionic surface active agent; a maximum of 0.01% (w/v) of benzalkonium chloride; a drug or a precursor or active substance; and optionally, one or more of the following components; isotonizing agents, viscosity modifying agents, stabilizers, buffers and/or antioxidants. The vehicle is prepared by emulsification of an aqueous phase which contains a non-ionic surface active agent with an organic phase containing dissolved therein an oil and the drug, drug precursor or active substance in an organic water miscible solvent and then totally removing by evaporation the organic solvent and part of the water up to the final desired volume. The vehicle is especially useful in ophthalmic preparations used to treat eye disorders and diseases.

16 Claims, 8 Drawing Sheets

NANOEMULSION OF THE OIL WATER TYPE, USEFUL AS AN OPHTHALMIC VEHICLE AND PROCESS FOR THE PREPARATION THEREOF

BACKGROUND OF THE INVENTION

1. Field of the Invention

The present invention fits in the field of the release of drugs, specifically for use in Ophthalmology, by means of oil in water type emulsion. The present invention provides a vehicle that produces an increase of the corneal penetration of the active substance included in the composition.

2. Description of the Related Art

For the treatment of eye disorders and diseases, the most commonly used vehicles are aqueous solutions. However, the aqueous solutions applied to the eye are rapidly diluted and eliminated as a result of delacrimation and the mechanical action of blinking, disappearing in a high proportion through the nasolacrimal duct. In this way, most of the drug administered is eliminated before it penetrates into the cornea and sclera giving rise to a low ocular bioavailability of the same.

On the other hand, many of the drugs that may be used in the eyes are of a lipophilic type and therefore are not very water soluble, therefore, they must be applied in the form of a suspension or ointment, which causes in some cases problems of irritation or discomfort after application. Besides, in the case of suspensions, the bioavailability is reduced due to the fact that it is necessary that the drug be dissolved in order to be absorbed before being eliminated from the eye surface.

Other types of vehicles have been developed for the purpose of increasing the permanence time of the drug on the eye surface. Among these are those that increase the bioavailability by means of an increase of the viscosity such as hydrogels or ophthalmic ointments. In the case of hydrogels, an important increase of the bioavailability of the drug has not been achieved. On their part, ophthalmic ointments have the large inconvenience of the awkwardness of their application and blurred vision that is produced after their application, the use thereof being more appropriate at night.

Likewise, a large number of novel vehicles have been developed such as liposomes, nanoparticles, etc., though most of them have problems of stability, tolerance, difficulties for industrialization thereof and even relative success as far as the increase of bioavailability is concerned.

Different types of emulsions have been suggested as vehicles for the release of drugs at the eye level.

Among these, patent application EP 0 521 799 A1 describes an oil in water type emulsion for the release of hydrophobic, amphiphilic and lipophilic drugs. Its composition comprises an oil, phospholipids and an amphoteric surface active agent. Although the role of phospholipids is essential for the stability of the emulsions of said invention, possible cataractogenic effects due to the phosphatidyl choline and, basically, to a derivative of the same, lysophosphatidyl, have been described by different authors. ((1) Effects of lysophosphatidyl choline and phospholipase A on the lens; Cotlier, E. Baskin, M. and Kresca L. Investigative Ophthalmology 14 (9): 697–701 (1975). (2) Phospholipid effects on the rat lens transport systems; Kador, P. F. and Kinoshita, J. H.; Exp. Eye Res. 26:657–665 (1978)).

On the other hand, the health authorities in most countries require the use of preservatives in ophthalmic products. This patent claims the use of the combination of thimerosal-chlorobutanol at a concentration of 0.01–0.2% (w/v) each, due to the lack of effectiveness thereof separately and of benzalkonium chloride 0.02% (w/v) when used individually.

The present invention provides an ophthalmic preparation in nanoemulsion form, which is stable in time without the need of including phospholipids in its composition. On the other hand, the preparations object of the present invention meet the requirements of the European, British and U.S. pharmacopeia, using a maximum of 0.01% (w/v) of benzalkonium chloride.

U.S. Pat. No. 5,171,566 describes an oil in water type emulsion, that comprises a soybean oil and soybean lecithin as an emulsifier. This type of emulsion, upon including lecithins, also contain phosphatidyl choline for which reason they may have the same problems of toxicity mentioned above. Likewise, they contain other stabilizers such as cholesterol or phosphatidic acid. This emulsion is lyophilized or it is to be kept at 4° C. This composition has the same inconveniences as the above cited patent and it comprises only flurbiprofen and the esters thereof. Unlike the present invention, it does not claim nor describe an action improving bioavailability, but rather it is limited to stating the presence of the drug in the aqueous humor in rabbits. On the other hand, we have observed that the nanoemulsion object of the present invention allows the bioavailability of the drug at the eye level to be increased approximately 4 times.

Patent application EP 0 480 690 A1, though it describes an emulsion type ophthalmic product, deals with a product that is substantially different from the object of the present invention. Said application claims the preparation of a microemulsion of tepoxaline whose aspect is that of a translucent to transparent formulation, inherent characteristic of microemulsions with a drop size of 0.005 to 0.5 µm. For the preparation of the same the use of sonification is required. This aspect greatly limits its industrial manufacturing. The non-ionic surface active agent used is a polysorbate and the concentration of the preservative(s) is from 0.02 to 0.7% (w/v). The present invention deals with a different composition since instead of a microemulsion it is a nanoemulsion neither transparent nor translucent (transmittance at 520 nm lower than 70%.) Likewise, the amount of preservative used is much less than that used in the previous patent, which is important due to the toxicity of preservatives at these concentrations.

SUMMARY OF THE INVENTION

The present invention provides an oil in water type emulsion type preparation that increases the bioavailability in the eye of the drug in the vehicle. Said emulsion is stable during storage without the need of including in its composition potentially irritating products and ones that can cause cataractogenic processes, such as the case of lecithins. Likewise, the formulation object of the present invention makes it possible to use minimum concentrations of the preservative (benzalkonium chloride) which in other types of formulations such as those mentioned above, do not meet the requirements of pharmacopeia for ophthalmic products. On the other hand, the emulsions of the present invention can be obtained with normal emulsification equipment, with a rotary agitator or else with a pressurized homogenizer.

Although in most countries health regulations require a preservative to be included in multidose type ophthalmic products, practically all of the preservatives used have substantial toxic effects at the eye level. Therefore, to have an ophthalmic vehicle that allows the use of low concentrations of preservative implies a very important advantage at the safety level of ophthalmic preparations. In this way, the present invention provides an ophthalmic vehicle that allows the use of low concentrations of a preservative (between 0.005% w/v and 0.01% w/v of benzalkonium chloride) unlike the compositions described in patent application EP 0 521 799 A1, which claims the use of the combination 0.01%–0.2% (w/v) of chlorobutanol and 0.01%–0.2% (w/v) of thimerosal, due to the lack of effectiveness of benzalkonium chloride at 0.02% (w/v) due to possible interactions with the surface active agents used or even due to the absorption thereof in the oil used.

DETAILED DESCRIPTION OF THE INVENTION

In accordance with the present invention, the oil soluble or partly oil soluble drugs are included in an oil in water type emulsion to be administered in the eye thus increasing the bioavailability of the same with regard to other compositions. Said vehicle comprises an oil and a non-ionic surface active agent, as well as enough preservative to meet the requirements of the pharmacopeia.

The oil that forms part of the emulsion may be a vegetable oil, an animal oil, a mineral oil, fatty acids, a medium chain triglyceride, fatty alcohols or any combination of these oils and oily substances that are well tolerated at the eye level.

The preferred oils are medium chain triglycerides due to their higher solubility in water, due to their density, because they are less susceptible to oxidation and due to their good tolerance at the eye level. Among these, fractionated $C_8$–$C_{10}$ fatty acid triglycerides of coconut oil, as well as $C_8$–$C_{10}$ medium chain saturated fatty acid propylenic glycol, stand out. Polyethylene glycol esters and glycerides should also be pointed out.

As vegetable oils, olive oil, sunflower seed oil and sesame seed soil with an acid value less than 0.5 are worth mentioning.

The oil is found in the compositions of the present invention preferably between 0.1 and 10% (w/v.)

Examples of non-ionic surface active agents are polyoxyethylene—polyoxypropylene copolymers, preferably polyoxamer 188 and poloxamer 407. These surface active agents are very well tolerated when administered in the eye, even at concentrations of 10% (w/v), not producing irritation nor lesions at the eye level. Use of these surface active agents at the suitable concentration makes it possible to keep the nanoemulsions stable without the need of using other co-surface active agents.

The concentration of the preferred non-ionic surface active agent for the compositions of the present invention is between 0.1 and 10% (w/v).

The composition of the present invention can contain different drugs used in Ophthalmology.

Examples of antiglaucomatous drugs can be carteolol base, betaxolol, atenolol, thymolol base and carbonic anhydrase inhibitors such as methazolamide.

An example of an antibiotic may be chloramphenicol; examples of anti-inflammatory drugs may be indomethacin, pyroxycam, dichlofenac acid, ibuprofen, dexamethasone and chlobetasone.

Other types of drugs are cyclosporin A, acyclovir and acid chromoglycate.

According to the nature of the oil, the composition of the present invention may contain an antioxidant to prevent oxidation of the same.

The composition of the present invention may contain an isotonizing agent such as mannitol, glycerol, sorbitol or glucose; viscosity modifying agents such as for example hydroxypropylmethylcellulose, polyacrylic acid derivatives or sodium carboxymethylcellulose; stabilizers such as sodium edatate and citric acid; buffers such as sodium phosphate and potassium phosphate, sodium citrate, sodium carbonate and sodium bicarbonate.

The use of polyacrylic acid polymers at some concentrations between 0.1 and 0.5% (w/v) stabilizes the compositions of the present invention avoiding coalescence of the oil droplets or even creaming of the separation of phases. These compositions have the apearance of a white gel with a certain consistency.

In accordance with the above, the present invention provides an oil in water type nanoemulsion useful as an ophthalmic vehicle, characterized in that it comprises:

(a) an oil in a proportion of approximately 0.1–10% (w/v);

(b) a non-ionic surface active agent in a proportion of approximately 0.1–10% (w/v);

(c) benzalkonium chloride as a preservative, in a proportion of approximately equal to or less than 0.01% (w/v);

(d) a drug, a drug precursor or a biologically active substance in a proportion of 0.01% to 5% (w/v);

(e) optionally, one or several of the following components: an isotonizing agent: a viscosity modifying agent; a stabilizer, a buffer and/or an antioxidant, in variable proportions;

The emulsion of the present invention shows a transmittance measured at 520 nm less than 70%, a pH between 5 and 8 and an osmolality between 250 and 400 mOsm/kg. The appearance of these emulsions tends to be light milky.

The compositions of the present invention may be sterilized by filtration when the droplet size allows it or they may be obtained sterile, by sterilization of the aqueous phase and the oily phase and subsequently mixing and emulsifying in aspectic conditions.

Contrary to what would be expected, the drug included in the composition of the present invention penetrates into an "in vitro" experimental model up to six times more through the cornea than the same drug in an aqueous solution. Likewise, when the composition of the present invention is instilled in a rabbit's eye "in vivo" levels of the drug in the aqueous humor almost four times higher than those obtained by aqueous solutions of the same drug are obtained.

This increase of bioavailability imparts a big advantage since in some cases it will allow the number of daily instillations or doses administered of those drugs used to treat chronic eye diseases to be reduced.

The composition of the present invention may be prepared in different ways. A process comprises the preparation separately of the aqueous and oily phases. The aqueous phase contains the non-ionic surface active agent in the suitable proportion, an isotonizing agent, a preservative and also a pH buffer system. The oily phase contains the active substance totally or partially solubilized in the oil and it can contain antioxidants.

For the preparation of the emulsion the oily phase is added to the aqueous phase under moderate agitation and subsequently the particle size is reduced by an Ultra-turrax type homogenizer (Janke and Kunkel, Staufen, Germany) until an average particle size smaller than 0.5 μm is obtained. Droplets of this size can also be obtained by using high pressure homogenizers or any other apparatus that allows the particle size to be adequately reduced.

Another particular preparation method of the present invention allows an oil in water type emulsion to be obtained with average size droplets of 200 nm at a temperature no higher than 35° C., unlike the normal processes that subject the product to temperatures between 45° and 85° C. which can affect the thermosenstitive active principles, or accelerate oxidation and decomposition reactions of the components of the formula.

This preparation method consists of preparing an aqueous phase in the same way as described above and an organic phase that comprises the active principle, totally or partially soluble in the oil, and the oil, both dissolved in a specific volume of an easily water miscible organic solvent and with a dielectric constant higher than 15, such as acetone, ethanol or tetrahydrofuran. Said organic phase is added to the aqueous phase under moderate agitation and the organic solvent and part of the water at reduced pressure are removed by a suitable evaporation system and at a temperature no higher than 35° C., obtaining a very fine and homogenous emulsion.

BRIEF DESCRIPTION OF THE DRAWINGS

1: Transcorneal penetration chamber
2: Thermostatted bath (37° C.)
3: Carbogen tank (95% $O_2$ and 5% $CO_2$)
4: Omniscribe D-5000 recorder
5: Pt-calomel electrodes
6: Agarose:KCl bridges
7: Amplifier
8: Peristaltic pump
9: Magnetic agitator
10: Artificial tear solution/test product

EXAMPLES

Figure 1:
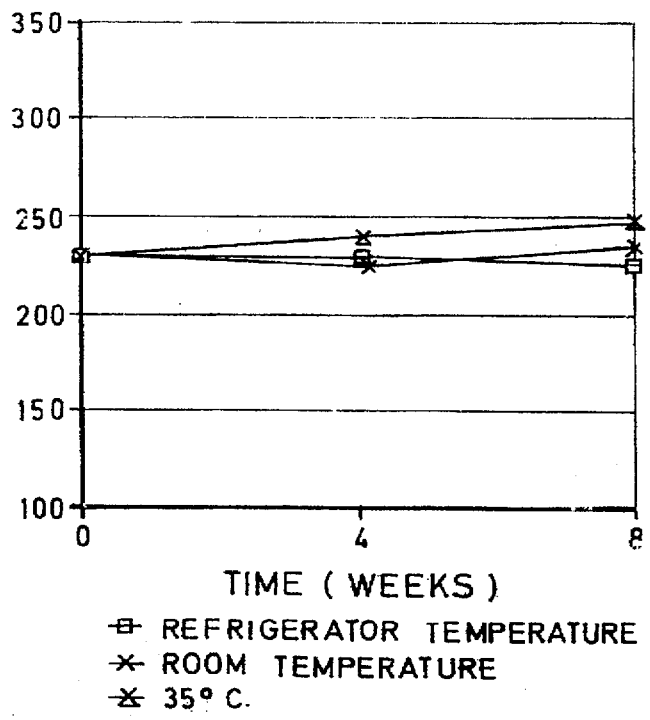
FIG. 1 is a graph that represents the study of the stability of Emulsion A in contrast to time, showing the results of the average size of the droplets in nm.

The present invention is additionally illustrated by the following examples, that must not be considered as restrictive of the scope of the same which is defined by the attached claim set.

For the description of the examples, the commercial names of the products are used. The products must be considered as any product with the same characteristics marketed by any other firm. The products are the following:

Miglyol 812® (Dynamit Nobel, Sweden): they are fractionated $C_8$–$C_{10}$ fatty acid triglycerides of coconut oil.

Edenor SbO₅® (Henkel, Dusseldorf): it is a mixture of saturated and unsaturated fatty acids where the main constituent is oleic acid (67%.)

Lutrol F68® (BASF, Germany): it is poloxamer 188 which is a polyoxyethylene-polyoxypropylene copolymer.

In all the formulations that are described hereinafter, the two phases are either sterilized separately and the emulsion is prepared aseptically or the final product is sterilized by 0.22 μm filter filtration.

EXAMPLE 1

NANOEMULSION OF MIGLYOL 812®
(EMULSION A)

10 g of the non-ionic surface active agent (Lutrol F68®) are added to 500 ml. of deionized water. 15 ml of oil (Miglycol 812®) are added to this solution. Then it is passed through an Ultra-turrax homogenizer (Janke and Kunkel, Staufen, Germany) for 20 minutes at 10,000 r.p.m. to emulsify it, obtaining a nanoemulsion with s size smaller than 0.5 μm. 0.25 g od disoidum edetate (stabilizer), 27.4 g. of sorbitol powder (isotonizing agent) and 0.05 g of benzalkonium chloride (preservative) are added to this emulsion. The resulting concentrations are:

| Lutrol F68 ®: | 2.00% (w/v) |
|---|---|
| Miglyol 812 ®: | 3.00% (v/v) |
| Disodium edetate: | 0.05% (w/v) |
| Sorbitol powder: | 5.48% (w/v) |
| Benzalkonium chloride: | 0.01% (w/v) |
| Deionized water q.s. | 100 ml |

The average size of the droplets measured in a Zetasizer 3 (Malvern Instruments, England) was 230 nm and the polydispersity was 0.220.

EXAMPLE 2

NANOEMULSION OF MIGLYOL 812®
(EMULSION B)

The technique described in example 1 is followed, but 20 g of Lutrol F68® are added instead of 10 g. The resulting concentrations are:

| Lutrol F68 ®: | 4.00% (w/v) |
|---|---|
| Miglyol 812'®: | 3.00% (v/v) |
| Disodium edetate: | 0.05% (w/v) |

| | |
|---|---|
| Sorbitol powder: | 5.48% (w/v) |
| Benzalkonium chloride: | 0.01% (w/v) |
| Deionized water q.s. | 100 ml |

The average size of the droplets measured in a Zetasizer 3 (Malvern Instruments, England) was 237 nm and the polydispersity was 0.241.

EXAMPLE 3

NANOEMULSION OF CARTEOLOL BASE 0.2% (EMULSION C)

8 g of Lutrol F68® are added to 190 ml of deionized water filtered through 0.22 µm up to the total solution of the former (aqueous phase). Separately, 0.42 g carteolol base are weighed to which 0.2 g of Edenor SbO$_5$® (Henkel) and 2.0 g of Miglyol 812® are added. It is heated gentle until the solution of the carteolol base (oily phase). The oily phase is added to the aqueous phase under magnetic agitation and then it is passed through the Ultra-turrax homogenizer (Janke and Kunke, Staufen, Germany) for 10 minutes at 10,000 r.p.m. until a nanoemulsion of a size smaller than 0.5 µm is achieved. This nanoemulsion thus formed has a basic pH that is neutralized up to a pH=7.4, with a 0.1N HCl solution 10.14 g. of apyrogenic mannitol are added to the previous emulsion to isotonize it and then 2 ml. of a benzalkonium chloride solution 1% (w/v) are added. Finally, the volume is completed up to 200 ml. with deionized water. The final concentrations are:

| | |
|---|---|
| Lutrol F68 ®: | 4.00% (w/v) |
| Miglyol 812 ®: | 1.00% (w/v) |
| Edenor SbO$_5$ ®: | 0.10% (w/v) |
| Carteolol base: | 0.22% (w/v) |
| Apyrogenic mannitol: | 5.07% (w/v) |
| Benzalkonium chloride: | 0.01% (w/v) |
| Deionized water q.s. | 100 ml |

The average size of the droplets measured in a Zetasizer 3 (Malvern Instruments, England) was 272 nm and the polydispersity was 0.273.

EXAMPLE 4

NANOEMULSION OF INDOMETHACIN 0.1% (EMULSION D)

1.66 g of Lutrol F68$^{200}$ are dissolved in 100 ml. of deionized water filtered through 0.22 µm (aqueous phase). 0.05 g of indomethacin and 0.5 g. of Miglyol 812® are dissolved in 50 ml. of acetone (organic phase): The organic phase is added to the aqueous phase under magnetic agitation at 500 r.p.m. The resulting dispersion is evaporated by a rotary vapor device at reduced pressure and at a temperature no higher than 35° C. until all the acetone and part of the water is eliminated and a final volume of 40 ml. is achieved. 2.53 g. of apyrogenic mannitol are added to isotonize it and 0.50 ml. of a banzaikonium chloride solution 1% (w/v) is added as a preservative. The buffer is prepared "in situ" by adding and dissolving 0.0025 g. of crystallized monopotassium phosphate and 0.1128 g of crystallized disodium phosphate 12 H$_2$O for a final pH of 7. 0.0275 g of disodium edetate are also added to the formula as a stabilizer and the volume is completed to 50 ml. with deionized water. The resulting concentrations are:

| | |
|---|---|
| Lutrol F68 ®: | 3.320% (w/v) |
| Miglyol 812 ®: | 1.000% (w/v) |
| Indomethacin: | 0.100% (w/v) |
| Apyrogenic mannitol: | 5.070% (w/v) |
| Cryst. monopotassium phosphate: | 0.005% (w/v) |
| Cryst. disodium phosphate 12 H$_2$O | 0.221% (w/v) |
| Disodium edetate: | 0.055% (w/v) |
| Benzalkonium chloride: | 0.010% (w/v) |
| Deionized water q.s. | 100 ml. |

The average size of the droplets measured in a Zetasizer 3 (Malvern Instruments, England) was 280 nm and the polydispersity was 0.250.

EXAMPLE 5

GEL WITH A NANOEMULSION OF MYGLYOL 812® (EMULSION E)

0.10 g. of Lutrol F68® are added to 15 ml. of deionized water filtered through 0.22 µm until the total solution of the former. 0.20 ml. of Myglyol 812® are added to this solution under magnetic agitation. Then, the resulting dispersion is passed through the Ultra-turrax homogenizer (Janket and Kunkel, Staufen, Germany) for 15 minutes at 10,000 r.p.m. to emulsify it, obtaining a nanoemulsion of size smaller than 0.5 µm. 1.014 g. of apyrogenic mannitol and 0.2 ml. of benzalkonium chloride solution 1% (w/v) are added to this emulsion. To complete the formula, 5 g. of Carbol 940 gel 0.6%, previously prepared, are added. It is stirred with a glass rod until a gel with the desired consistency is obtained. The resulting concentratons are:

| | |
|---|---|
| Lutrol F68 ®: | 0.50% (w/v) |
| Miglyol 812 ®: | 1.00% (w/v) |
| Apyrogenic mannitol: | 5.07% (w/v) |
| Benzalkonium chloride: | 0.01% (w/v) |
| Carbopol 940: | 0.15% (w/v) |
| Deionized water q.s. | 100 ml. |

The average size of the droplets measured in a Zetasizer 3 (Malvern Instruments, England) was 278 nm and the polydispersity was 0.259.

EXAMPLE 6

NANOEMULSION OF MIGLYOL 812® (EMULSION F)

4.00 g. of Lutrol F68® are added to 190 ml of deionized water filtered through 0.22 µm up to the total solution thereof. Once dissolved, the resulting aqueous phase is placed in a bath at 70° C. Once it is at the cited temperature, 6.00 ml. of Miglyol 812® are added. The resulting dispersion is passed through the Ultra-turrax homogenizer (Janke and Kunkel, Staufen, Germany) for 15 minutes at 10,000 r.p.m. until an emulsion with a size smaller than 0.5 µm is obtained. Then, 10.96 g. of sorbitol powder, 0.10 g. of disodium edetate and 1 ml. of benzalkonium chloride solution 1% (w/v) are added. Finally, the volume is completed to 200 ml. with deionized water. The final concentrations are:

| | |
|---|---|
| Lutrol F68 ®: | 2.000% (w/v) |
| Miglyol 812 ®: | 3.000% (w/v) |
| Sorbitol powder: | 5.480% (w/v) |

-continued

| | |
|---|---|
| Disodium edetate: | 0.050% (w/v) |
| Benzalkonium chloride: | 0.005% (w/v) |
| Deionized water q.s. | 100 ml. |

The average size of the droplets measured in a Zetasizer 3 (Malvern Instruments, England) was 224.3 nm and the polydispersity was 0.175.

EXAMPLE 7

NANOEMULSION OF MIGLYOL 812® (EMULSION G)

0.5 g. of Lutrol F68® are added to 90 ml. of deionized water filtered through 0.22 µm until the solution thereof. Once dissolved, the resulting aqueous phase is placed in a bath at 70° C. Once this is at the cited temperature 1.00 ml. of Miglyol 812® added. The resulting dispersion is passed through the Ultra-turrax homogenizer (Janke and Kunkel, Staufen, Germany) for 10 minutes at 10,000 r.p.m. until an emulsion with a size smaller than 0.5 µm is obtained. Then, 5.48 g. of sorbitol powder and 1 ml. of a benalkonium chloride solution 1% (w/v) are added. Then the volume is completed to 10 ml. with deionized water. The final concentrations are:

| | |
|---|---|
| Lutrol F68 ®: | 0.50% (w/v) |
| Miglyol 812 ®: | 1.00% (v/v) |
| Sorbitol powder: | 5.48% (W/v) |
| Benzalkonium chloride: | 0.01% (w/v) |
| Deionized water q.s. | 100 ml. |

STABILITY STUDIES

Figure 2:
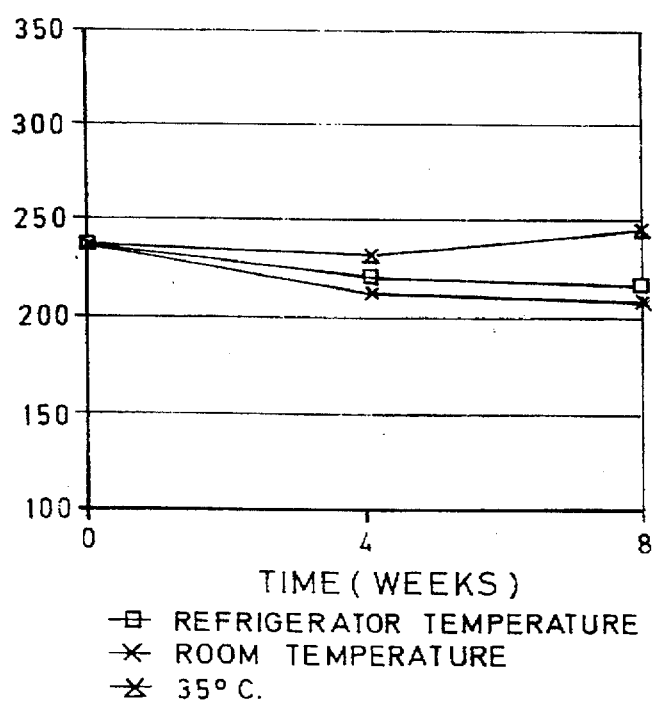
FIG. 2 is a graph that represents the study of the stability of Emulsion B in contrast to time, showing the results of the average size of the droplets in nm.
Figure 3:
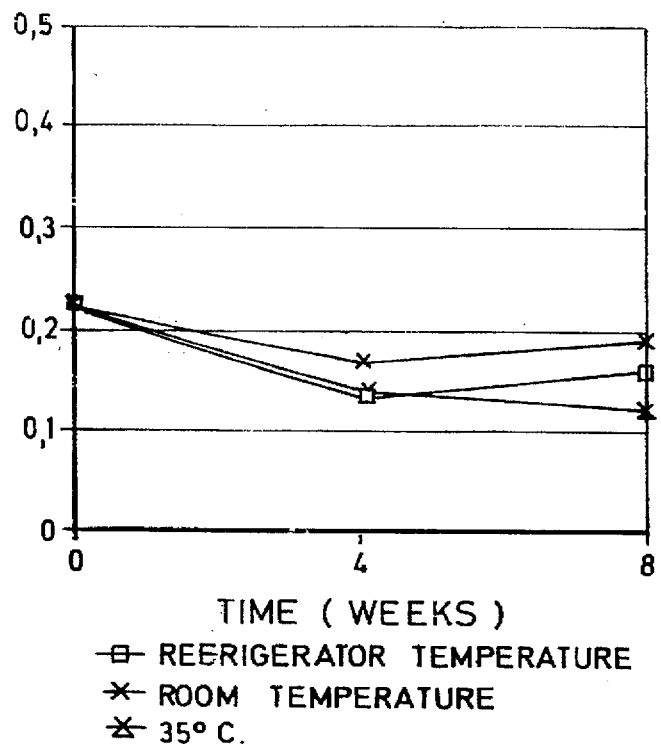
FIG. 3 is a graph that represents the study of the polydispersity of Emulsion A in contrast to time.
Figure 4:
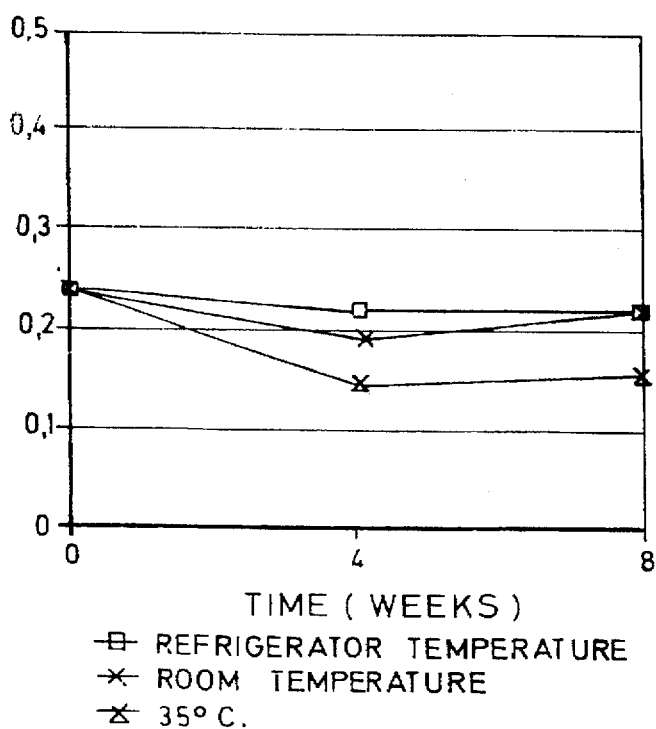
FIG. 4 is a graph that represents the study of the polydispersity of Emulsion B in contrast to time.
Figure 5:
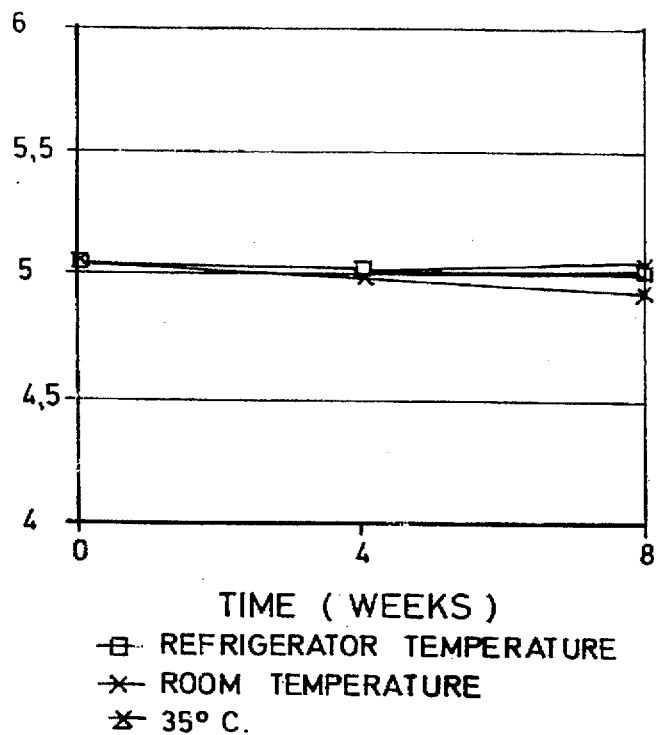
FIG. 5 is a graph that represents the study of the pH of Emulsion A incontrast to time.
Figure 6:
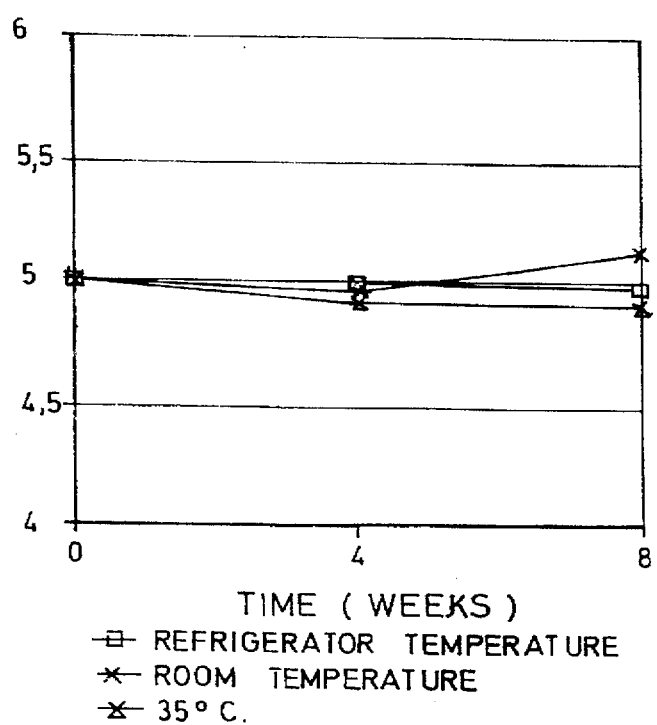
FIG. 6 is a graph that represents the study of the pH of Emulsion B in contrast to time.

The stability of emulsion A and of emulsion B kept at different temperatures has been followed up. Controls have been carried out at different time periods and the results of the average size of the droplets are shown in FIGS. 1 and 2 and the results of the polydispersity are shown in FIGS. 3 and 4. The results of the pH are shown in FIGS. 5 and 6. No significant change is observed in any of the three parameters studied throughout time.

Figure 7:
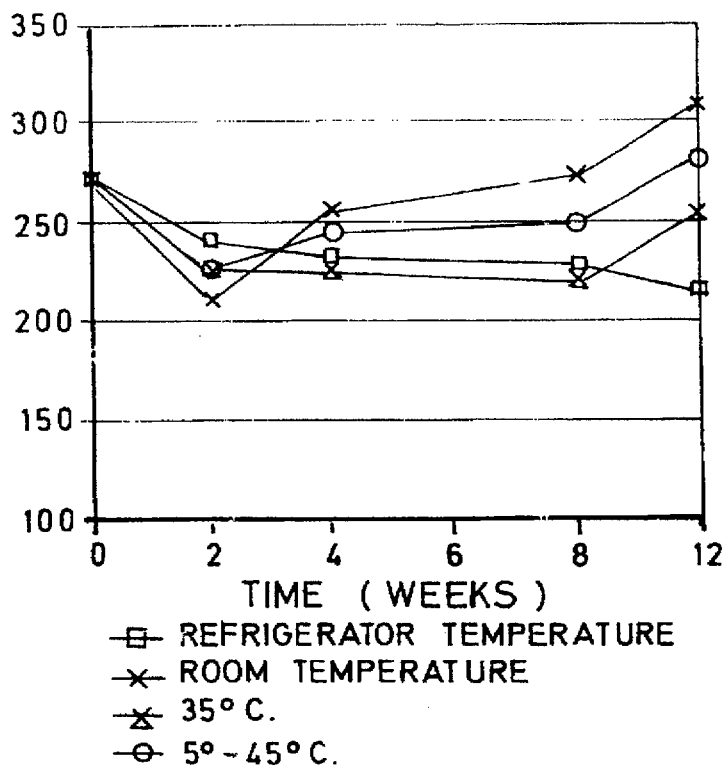
FIG. 7 is a graph that represents the study of the stability of Emulsion C in contrast to time, showing the results of the average size of the droplets in nm.
Figure 8:
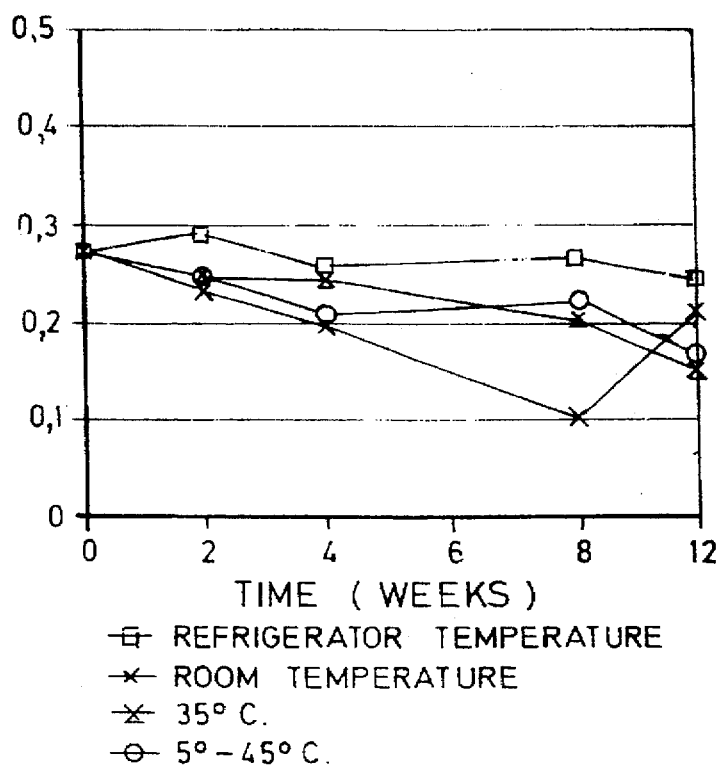
FIG. 8 is a graph that represents the study of the polydispersity of Emulsion C in contrast to time.
Figure 9:
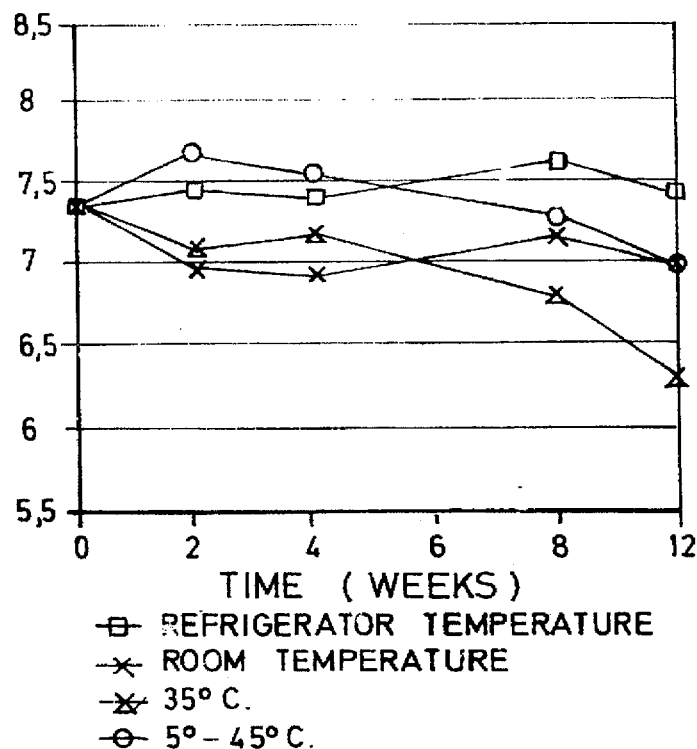
FIG. 9 is a graph that represents the study of the pH of Emulsion C in contrast to time.
Figure 10:
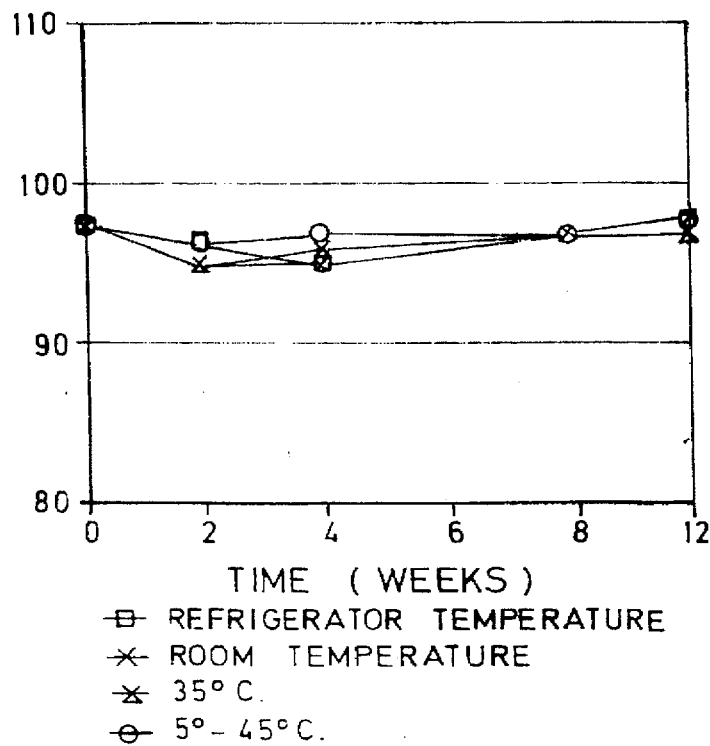
FIG. 10 is a graph that represents the study of the evolution of the content of active principle of Emulsion C in contrast to time, in percentage with regard to the initial theoretical content.

In nanoemulsion C, with carteolol base, aside from the above mentioned parameters the active principle content was also controlled. The results of the average size are shown in FIG. 7; the results of the polydispersity are shown in FIG. 8 and the results of the pH are shown in FIG. 9. As to the results of the active principle content, they are shown in FIG. 10. No important changes are observed in the physico-chemical parameters. As one can see in FIG. 10, there are no changes in the carteolol base concentration either during the storage period at the refrigerator temperature, room temperature, 35° C. and 5° C.–45° C. (alternation).

STUDY OF ACUTE EYE TOLERANCE IN RABBITS

The acute eye tolerance of emulsion B and of emulsion D was evaluated in New Zealand albino rabbits by means of repeated instillation of 50 µl every 20 minutes for 6 hours, using saline solution as the control. The eye tolerance was evaluated according to blinking, reddening, edema, exudation and lesions in the iris and cornea, once the applications were finished and after 24 hours had gone by.

The results obtained indicate that emulsion B as well as emulsion D have a correct eye irritation index.

"IN VITRO" TRANSCORNEAL PENETRATION

Figure 11:
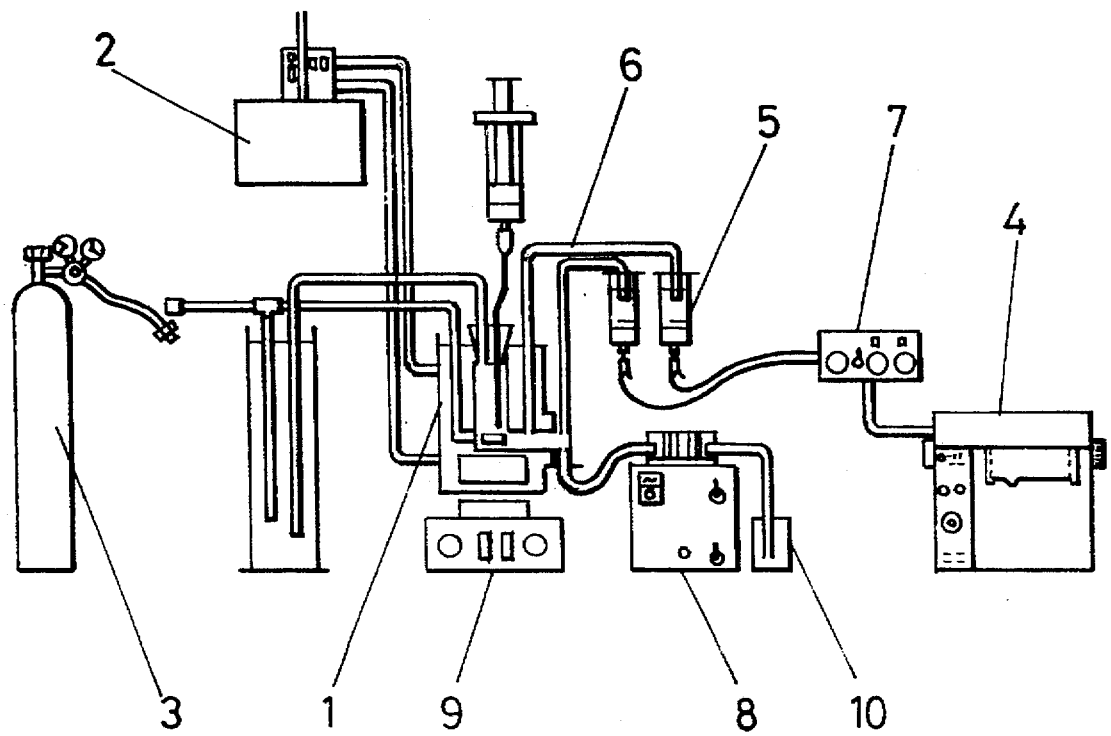
FIG. 11 is a diagram of the transcorneal penetration equipment (Model LC-100) used in the "in vitro" tests that are stated hereinafter. The corresponding numerical references have the following meanings.

The transcorneal penetration of the indomethacin in Nanoemulsion D at 0.1% (w/v) was determined and it was compared with the penetration of indomethacin 0.1% (w/v) in an aqueous solution. For this purpose, rabbit corneas were placed in the Transcorneal Penetration Chamber LC-100 according to Diez-Noguera et al. ((3) Diez-Noguera A., Igual A. and Guzmán L. Design of an "in vitro" system for pharmacokinetic studies, Labs. CUSI, S. A., El Masnous, Barcelona, Catalonia, Spain. 7th. International Congress of Eye Research, Nagoya, Japan (1986)) (FIG. 11). The epithelial surface of the cornea was exposed to the test product for 3 hours.

200 µl aliquots of artificial aqueous humor (AAH) were extracted from the rear part of the chamber after 15, 30, 60 120, 150 and 180 minutes. Wach sample was immediately replaced with an equal volume of AAH.

The indomethacin content of the samples was determined immediately after extraction by HPLC at 250 nm and the values obtained were used to calculate the permeability coefficient (P, in cm/s).

| | Permeability Coefficient $(cm/s) \times 10^{-6}$ | Latency Time (min) |
|---|---|---|
| INDO | $2.5 \pm 0.2$ | $78 \pm 1$ |
| NAND | $16.0 \pm 0.8$ | $45 \pm 3$ |

INDO: Indomethacin solution 0.1% (w/v)
NAND: Nanoemulsion D

Figure 12:
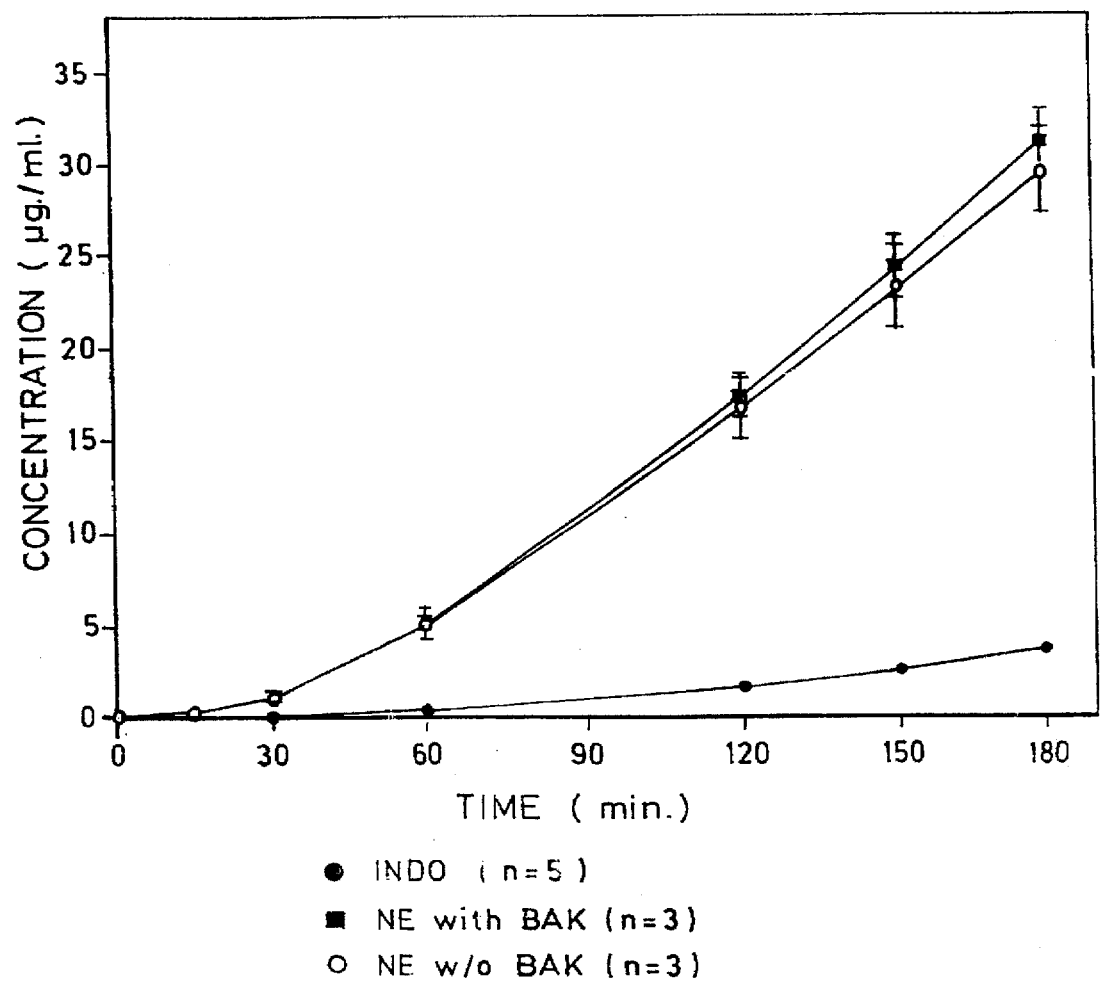
FIG. 12 is a graph that represents the transcorneal penetration studies on indomethacin in the nanoemulsion D, showing the concentration of the same in contrast to time.

The results are expressed graphically in FIG. 12.

The permeability coefficient was calcuated using the equation according to Grass and Robinson ((4) Grass G. M., and Robinson J. R. (1988) Journal of Pharmaceutical Sciences Vol. 77, no 1, 3–14):

$$P = \frac{\Delta L}{\Delta t} \cdot \frac{3}{60 \cdot A \cdot Co}$$

wherein $\frac{\Delta t}{\Delta L}$ = slope of the rectilineal portion of the graph 3=volume in ml of the rear surface of the chamber
60=conversion of minutes into seconds
A=corneal surface exposed to the product (0.721 cm)
Co=theoretical concentration of the test product The latency time was obtained by extrapolation of the rectilineal portion of the graph.

As one can see in FIG. 16, the indomethacin in the nanoemulsion penetrates before and in larger proportion than when it is in an aqueous solution.

"IN VIVO" PHARMACOKINETIC STUDIES

Pigmented rabbits (Fauver de Bourgonge) were bilaterally treated with a single instillation of 25 µl of nanoemulsion D and of the aqueous indomethacin solution 0.1% (w/v). Approximately 200 µl of aqueous humor from the front chamber were obtained 15, 30 minues and 1, 2, 4, 6 and 8 hours after instillation.

The aqueous humor samples were filtered through an 0.45 µm filter and analyzed by HPLC at 250 nm immediately after extraction.

The results obtained were the following:

|      | Cmax (ng/ml) | Tmax (min) | Kabs (h$^{-1}$) | Latency t. (min) | T ½ β (h) | AUC (ng. min/ml) | AUC$_{NAND}$/AUC$_{INDO}$ |
|------|------|------|------|------|------|------|------|
| INDO | 144 | 53 | 2.8 | 10 | 1.2 | 22853 | 1 |
| NAND | 314 | 68 | 1.4 | 2 | 1.3 | 79223 | 3.5 |

INDO: Indomethacin solution 0.1% (w/v)
NAND: Nanoemulsion D
T ½ β: average elimination half-life The results are expressed graphically in FIG. 13.

Figure 13:
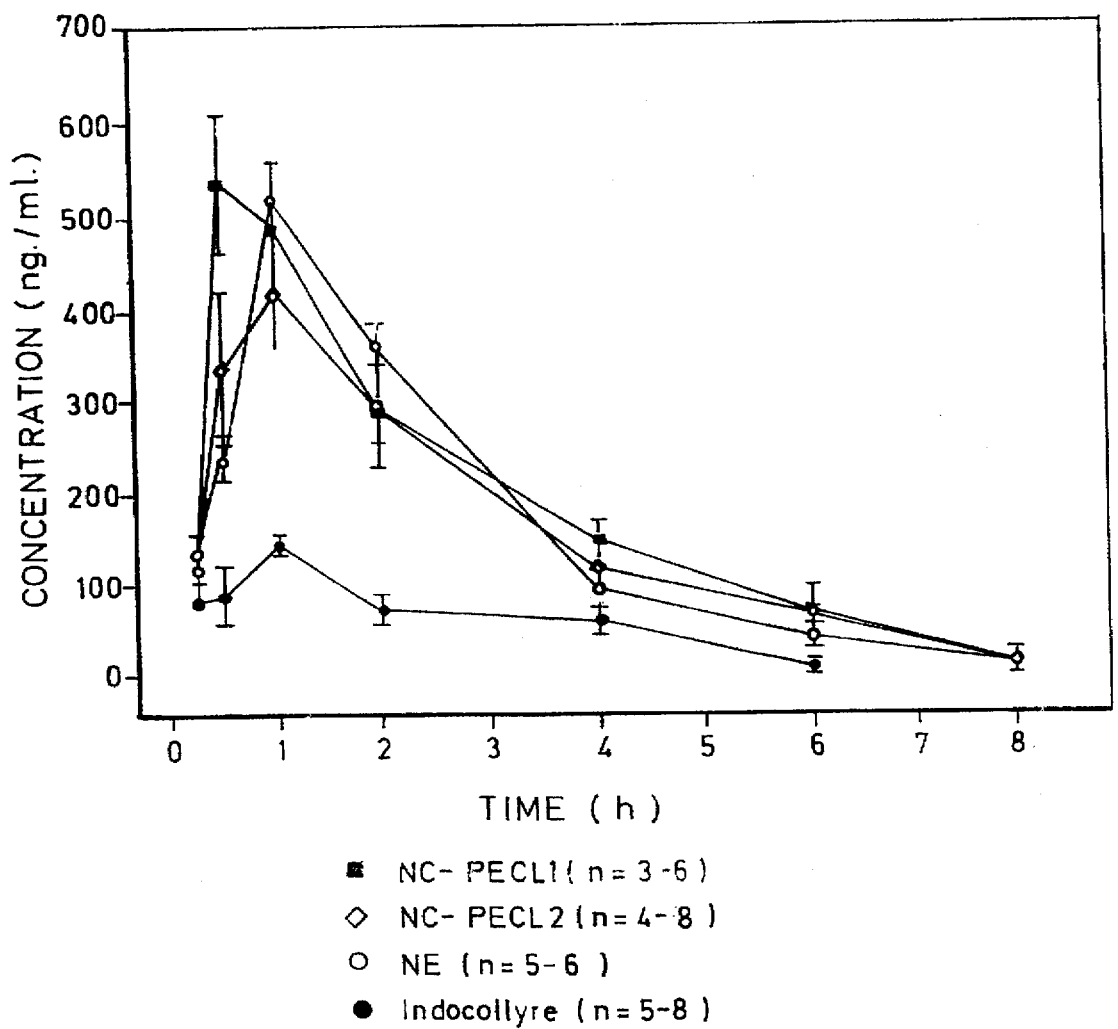
FIG. 13 is a graph that represents the "in vivo" pharmacokinetic studies on the nanoemulsion D, showing the concentration values of indomethacin in the rabbit's pigmented aqueous humor in contrast to time.

As one can see in FIG. 13, the experimental data show a very significant increase of penetration of the indomethacin of nanoemulsion D with regard to the aqueous solution. Likewise, the presence of indomethacin in the aqueous humor was prolonged two hours above the detection limit in nanoemulsion D with regard to the aqueous solution.

PRESERVATIVE EFFECTIVENESS STUDIES

The bacteria were cultured in Tryptose-soybean in an oven at 34° C. for 18 hours. *Candida albicans* and *Aspergillus niger* in Sabouraud's culture medium in an oven at 22° C. for 48 hours and 7 days respectively. From the culture media a suspension of approximately 1×10$^8$ ufc/ml. was made 200 μl of each one of the microorganism suspensions were added to tubes that contained 20 ml. of each one of the nanoemulsions (A, F and G). Counts were made of ufc of the microorganisms contained in 1 ml. of nanoemulsion at 0, 6, 24 hours and 7, 14 and 28 days. Besides, the ufc count of the microorganisms in physiological saline solution was done as an inoculum control and the sterility control of the medium without inoculation was carried out. For each ml of nanoemulsion and for each time tested, a series of dilutions (1/19) in Leethan broth with 0.5% (w/v) of Tween 80 added to neutralize the preservative, was made. 1 ml. of each dilution was grown, in triplicate, in 20 ml. of tryptose agar soybear melt at 45° C. and Tween 80 0.5% (w/v) added.

Nanoemulsions A and F meet the requirements for ophthalmic preparations of the European Pharmacopoeia 1993 (criterion B) and British Pharmacopoeia 1993 (criterion B); Farmacopeé Francaise 1989 and U.S.P. XXII 1990. The smaller content of surface active agent in nanoemulsion G also permits the requirements of European Pharmacopoeia 1993 (criteirion A) and British Pharmacopoeia 1993 (criterion A) to be met. Therefore, the nanoemulsions of the present invention meet the criteria of the most important pharmacopoeia with a concentration of preservative much lower than that used in other oil in water type emulsions, which do not meet the requirements of pharmacopoeia with regard to preservative effectiveness using the concentrations of preservatives used in the formulations of the present invention.

The results are shown on Tables 1, 2 and 3.

TABLE 1

EMULSION F

| Microorganism | Inoculum ufc/ml 0 hours | Colony forming units-time after inoculation | | | | | |
|---|---|---|---|---|---|---|---|
| | | 0 hours | 6 hours | 24 hours | 7 days | 14 days | 28 days |
| *Pseudomonas aeruginosa* ATCC 9027 | 8.3 × 10$^5$ | 1.3 × 10$^5$ | <10 | <10 | <10 | <10 | <10 |
| *Escherichia coli* ATCC 8739 | 1.2 × 10$^6$ | 1.3 × 10$^6$ | — | — | 3.3 × 10$^1$ | <10 | <10 |
| *Staphylococcus aureus* ATCC 6538 P | 1.0 × 10$^6$ | 3.8 × 10$^5$ | 5.1 × 10$^3$ | 7.0 × 10$^1$ | <10 | <10 | <10 |
| *Candida albicans* ATCC 10231 | 1.7 × 10$^6$ | 1.1 × 10$^6$ | — | — | 2.1 × 10$^5$ | 1.6 × 10$^5$ | 1.2 × 10$^5$ |
| *Aspergillus niger* ATCC 16404 | 1.5 × 10$^5$ | 1.8 × 10$^5$ | — | — | <10 | 4.7 × 10$^1$ | <10 |
| Media control | TSA | — | — | — | — | | |
| | SDA | — | — | — | — | | |

TABLE 2

EMULSION A

| Microorganism | Inoculum ufc/ml 0 | Colony forming units-time after inoculation | | | | | |
|---|---|---|---|---|---|---|---|
| | | 0 hours | 6 hours | 24 hours | 7 days | 14 days | 28 days |
| *Pseudomonas aeruginosa* ATCC 9027 | 8.3 × 10$^5$ | 9.0 × 10$^3$ | <10 | <10 | <10 | <10 | <10 |
| *Escherichia coli* ATCC 8739 | 1.2 × 10$^6$ | 6.5 × 10$^5$ | — | — | <10 | <10 | <10 |
| *Staphylococcus aureus* | 1.0 × 10$^6$ | 2.6 × 10$^5$ | 1.4 × 10$^2$ | 8.0 × 10$^1$ | <10 | <10 | <10 |

TABLE 2-continued

EMULSION A

| Microorganism | Inoculum ufc/ml 0 | Colony forming units-time after inoculation | | | | | |
|---|---|---|---|---|---|---|---|
| | | 0 hours | 6 hours | 24 hours | 7 days | 14 days | 28 days |
| ATCC 6538 P | | | | | | | |
| Candida albicans ATCC 10231 | $1.7 \times 10^6$ | $1.0 \times 10^6$ | — | — | $4.4 \times 10^4$ | $4.3 \times 10^2$ | <10 |
| Aspergillus niger ATCC 16404 | $1.5 \times 10^5$ | $6.4 \times 10^4$ | — | — | $1.4 \times 10^2$ | <10 | <10 |
| Media control | TSA | — | — | — | — | | |
| | SDA | — | — | — | — | | |

TABLE 3

EMULSION G

| Microorganism | Inoculum ufc/ml 0 | Colony forming units-time after inoculation | | | | | |
|---|---|---|---|---|---|---|---|
| | | 0 hours | 6 hours | 24 hours | 7 days | 14 days | 28 days |
| Pseudomonas aeruginosa ATCC 9027 | $1.3 \times 10^6$ | $2.7 \times 10^5$ | <10 | <10 | <10 | <10 | |
| Escherichia coli ATCC 8739 | $1.0 \times 10^6$ | $5.7 \times 10^4$ | — | — | <10 | <10 | |
| Staphylococcus aureus ATCC 6538 P | $1.0 \times 10^6$ | $9.3 \times 10^5$ | <10 | <10 | <10 | <10 | |
| Candida albicans ATCC 10231 | $1.0 \times 10^6$ | $6.6 \times 10^2$ | — | — | <10 | $2.1 \times 10^2$ | |
| Aspergillus niger ATCC 16404 | $3.0 \times 10^5$ | $7.2 \times 10^4$ | — | — | <10 | <10 | |
| Media control | TSA | — | — | — | — | — | |
| | SDA | — | — | — | — | — | |

What is claimed is:

1. A nanoemulsion comprised of droplets having oil cores, useful as an ophthalmic vehicle, obtained by preparing an emulsion of an aqueous phase in an oil phase, said oil phase comprising an oil in an amount of 0.1–10% in which at least one of a drug, a drug precursor or a biologically active substance in an amount of 0.01–5% (w/v) is totally or partially solubilized therein; and, optionally, an antioxidant;

said aqueous phase comprising a water-miscible non-ionic surface active agent in an amount 0.1–10% (w/v) and benzalkonium chloride in a maximum amount of 0.01% (w/v);

said aqueous phase optionally containing additives selected from the group consisting of isotonizing agents, viscosity modifying agents, stabilizers and buffers;

said drug, drug precursor or biologically active substance being contained in the oil cores of the nanodroplets of the resultant nanoemulsion;

said nanoemulsion having a transmittance at 520 nm of less than 70%, a pH between 5 and 8; and an osmolarity between 250 and 400 mOsm/kg.

2. A process for the preparation of the oil in water nanoemulsion of claim 1, which comprises the steps of:

preparing an aqueous phase containing a water-miscible non-ionic surface active agent, benzalkonium chloride in a maximum amount of 0.01% (w/v), and, optionally, additives selected from the group consisting of isotonizing agents, buffers, preservatives, viscosity modifying agents and stabilizers;

preparing an oil and a substance selected from at least one of the group consisting of drugs, drug precursors, biologically active substances or mixtures thereof, said substance being totally or at least partially solubilized in the oil;

dissolving said oil and said substance in an organic, easily water miscible solvent having a dielectric constant higher than 15 to form an organic phase;

adding said organic phase to the aqueous phase under moderate agitation so as to obtain a nanoemulsion;

removing the organic phase and part of the water at reduced pressure and a temperature not higher than 35° C., to obtain a homogenous nanoemulsion with droplets having an average particle size of approximately 200 nm.

3. A nanoemulsion according to claim 1, wherein the oil is a fractionated fatty acid triglyceride of coconut oil, a mixture of fatty acids or a propylenic glycol ester of saturated vegetable fatty acids.

4. A nanoemulsion according to claim 1, wherein the non-ionic surface active agent is a polyoxyethylene—polyoxypropylene copolymer.

5. A nanoemulsion according to claim 4, wherein the non-ionic surface active agent is a poloxamer.

6. A nanoemulsion according to claim 1, wherein the drug is selected from the group consisting of antiglaucomatous drugs, antibiotics, antiallergic drugs, antiviral drugs and anti-inflammatory drugs.

7. A nanoemulsion according to claim 6, wherein the antiglaucomatous drug is selected from the group consisting carteolol base, betaxolol, atenolol and thymolol base.

8. A nanoemulsion according to claim 6, wherein the anti-inflammatory drug is selected from the group consisting of indomethacin, pyroxycam, dichlofenac acid, ibuprofen, dexamethasone and chlobetasone.

9. A nanoemulsion according to claim 6, wherein the drug is cyclosporin A.

10. A nanoemulsion according to claim 6, wherein the drug is acyclovir.

11. A nanoemulsion according to claim 6, wherein the drug is acid chromoglygate.

12. A nanoemulsion according to claim 3, wherein the isotonizing agent is selected from the group consisting of mannitol glycerol, sorbitol and glucose.

13. A nanoemulsion according to claim 1, wherein the viscosity modifying agent is selected from the group consisting of hydroxypropylmethylcellulose, polyacrylic acid derivatives or sodium carboxymethylcellulose.

14. A nanoemulsion according to claim 1, wherein in that the stabilizer is selected from the group consisting of sodium ethyenediamino-tetraacetate and citric acid.

15. A nanoemulsion according to claim 1, wherein the buffer is selected from the group consisting of sodium phosphate, potassium phosphate, sodium citrate, sodium carbonate and sodium bicarbonate.

16. Nanoemulsion according to claim 1, characterized in that the benzalkonium chloride is found in a concentration equal to or less than 0.005% (w/v).

* * * * *